United States Patent [19]
Dill et al.

[11] Patent Number: 5,495,851
[45] Date of Patent: Mar. 5, 1996

[54] USE OF ENDOSCOPIC ULTRASOUND AND STIMULATED BILARY DRAINAGE IN THE DIAGNOSIS OF CHOLECYSTITIS AND MICROLITHIASIS

[75] Inventors: James E. Dill, Goodview; Linda Berkhouse, Roanoke, both of Va.

[73] Assignee: Roanoke Gastroenterology, P.C., Roanoke, Va.

[21] Appl. No.: 409,177

[22] Filed: Mar. 23, 1995

[51] Int. Cl.$^6$ ..................................... A61B 8/00
[52] U.S. Cl. ........................................ 128/660.03
[58] Field of Search ............... 128/660.01, 660.03, 128/662.05; 601/2, 4; 604/51; 600/101, 160

[56] References Cited

U.S. PATENT DOCUMENTS

| | | | |
|---|---|---|---|
| 3,937,819 | 2/1976 | Ondetti et al. | 424/177 |
| 4,917,095 | 4/1990 | Fry et al. | 128/660.03 |
| 4,979,496 | 12/1990 | Komi | 128/4 |
| 5,250,025 | 10/1993 | Sosnowski et al. | 604/51 |

OTHER PUBLICATIONS

Pentax Endoscopic Ultrasound Brochure, "The Next Generation".
Hitachi Medical Brochure, EUB 515 Plus, Digital Ultrasound System.
Ultrasound Scanner Endoscope Brochure, Hitachi EUB 515A and Pentax FG-32UA.
Sincalide, AHFS Drug Information, 1994, from Bristol-Myers/Squibb.
Dahan et al., "Is Endoscopic Ultrasonography (EUS) Helpful in Patients with Suspicion of Complicated Gallstones and Normal Ultrasonography US?", SGA Abstract, May 1993 Meeting.
T. Rosch and M. Classen, Gastroenterologic Endosonography, pp. 1–12, Thieme Medical Publishers, Inc., 1992.

*Primary Examiner*—George Manuel
*Attorney, Agent, or Firm*—Ohlandt, Greeley, Ruggiero & Perle

[57] ABSTRACT

The combined endoscopic ultrasound and stimulated biliary drainage method involves the following steps: inserting an endoscopic ultrasound device within the antrum of a stomach; positioning the endoscopic ultrasound device within the stomach such that the endoscopic ultrasound device is allowed to have a substantially unobstructed view of the gallbladder; activating the endoscopic ultrasound device such that it is capable of detecting whether the gallbladder exhibits any of the following: gallbladder sludge or small gallstones, focal wall thickening, or adhesions about the gallbladder and/or cystic duct; delivering a cholecystokinin analogue intravenously to the human to enable the gallbladder to contract and to produce an ejection fraction of bile from the gallbladder during each contraction thereof; determining the degree of contraction of the gallbladder by means of measuring each the ejection fraction of the gallbladder; and removing the ejection fractions from the patient and analyzing the ejection fractions to detect the presence or absence of calcium bilirubinate and/or cholesterol granules or crystals therein; whereby cholecystitis or microlithiasis of a gallbladder can be diagnosed with an accuracy or sensitivity of between about 90% to 98%.

36 Claims, 1 Drawing Sheet

USE OF ENDOSCOPIC ULTRASOUND AND STIMULATED BILIARY DRAINAGE IN THE DIAGNOSIS OF CHOLECYSTITIS AND MICROLITHIASIS

The present invention generally relates to a method which is capable of accurately diagnosing cholecystitis and microlithias. This method is particularly useful when conventional transabdominal ultrasound tests produce a negative result and the patient continues to suffer from right upper quadrant abdominal pain. In particular, the present invention combines endoscopic ultrasound and stimulated biliary drainage, utilizing an intravenously delivered CCK analogue or an intraluminally delivered magnesium sulfate, to diagnose cholecystitis and microlithias with an accuracy of up to about 98%.

BACKGROUND OF THE INVENTION

The diagnosis and at times the treatment of recurring right upper quadrant abdominal pain can be quite difficult. All physicians deal with patients having pain in this area and in whom the usual diagnostic tests are negative. The conditions that can cause right upper quadrant pain are multiple. A partial list includes cholecystitis, cholelithiasis (i.e., microlithias), irritable bowel syndrome, esophagitis, biliary dyskinesia and right lower lobe pneumonitis.

Transabdominal ultrasound (TUS) has been considered the "gold standard" in the diagnosis of cholecystitis and choletithiasis until fairly recently. However, the diagnosis of cholecystitis and choletithiasis has proved difficult even when a transabdominal ultrasound instrument is used. As such, many patients experiencing recurring right upper quadrant abdominal pain due to cholecystitis or choletithiasis simple go undiagnosed and continue to explore other reasons for their discomfort.

In an article by Dahan P., et al., Is Endoscopic Ultrasonography (EUS) Helpful in Patients with Suspicion of Complicated Gallstones and Normal Ultrasonography (US), AGA Abstracts, April 1993, pg. A358, it was initially reported that endoscopic ultrasound (EUS) has a sensitivity of 81% in diagnosing cholecystitis in patients with negative transabdominal ultrasound examinations. Dahan et al. further disclosed the use of intramuscular cholecystokinin (CCK) to facilitate biliary drainage in patients when their EUS was negative.

Subsequently, Amouyal, et al., Value of Endoscopic Ultra Sonography in the Diagnosis of Idiopathic Acute Pancreatitis, Gastroenterology, April 1994, Vol. 106, No. 4, Pancreatic Disorders A283, discovered that endoscopic ultrasonography was accurate in demonstrating minilithiasis in the gallbladder in patients with acute idiopathic pancreatitis. In an article by Indaram, S. Channapragrade, A Retrospective Analysis of the Role of Endoscopic Ultrasound in the Evaluation of Gallbladder Diseases, Gastrointestinal Endoscopy No. 200, Vol. 40, No. 2, Part 2, March/April 1994, acalculous cholecystitis with thick sludge or choletithiasis was found in 16 out of 25 patients on endoscopic ultrasound, i.e., 64% sensitivity.

Although combined endoscopic ultrasound and stimulated biliary drainage has been used to diagnose cholecystitis in patients who otherwise would go undetected, it would be highly desirable to develop a diagnostic procedure which would significantly improve such diagnosis from the 81% sensitivity or success rates disclosed in the literature.

The present inventors have developed a unique diagnostic procedure which allows for the use of endoscopic ultrasound and stimulated biliary drainage using an intravenously delivered cholecystokinin analogue in the diagnosis of cholecystitis with an accuracy or sensitivity as high as about 98%. The standardized positioning of the ultrasound transducer in the gastric antrum, movement of the transducer against the stomach wall such that the ultrasound has a full view of the gallbladder, calculation of gallbladder ejection fraction, measuring the contractions of the gallbladder, and ejection of bile fractions using intravenous Kinevac™, a cholecystokinin analogue, manufactured by Bristol-Myers Squibb, all combine to provide a higher accuracy or sensitivity rate than earlier combined EUS and biliary drainage methods. One problem discovered with the earlier EUS diagnostic procedures is that they provided cholecystokinin (CCK) intramuscularly which does not appear to cause contraction of the gallbladder which is one of the techniques used by the present inventors to greatly improve the sensitivity of their diagnostic procedure. Two additional diagnostic steps of the present invention which also contribute to the high accuracy or sensitivity of this diagnostic procedure are the visualization of sludge in the gallbladder on endoscopic ultrasound, combined with searching for cholesterol crystals or calcium bilirubinate granules in the ejected bile fractions microscopically. Still other steps which assist in this diagnosis are focal wall thickening, calculation of ejection fractions, and the presence of adhesions.

The present invention also provides many additional advantages which shall become apparent as described below.

SUMMARY OF THE INVENTION

The combined endoscopic ultrasound and stimulated biliary drainage, utilizing an intravenous delivered CCK analogue, involves the following steps: inserting an endoscopic ultrasound device within the antrum of a stomach; positioning the endoscopic ultrasound device within the stomach such that the endoscopic ultrasound device is allowed to have a substantially unobstructed view of the gallbladder; activating the endoscopic ultrasound device such that it is capable of detecting whether the gallbladder exhibits any of the following: gallbladder sludge, small gallstones, focal wall thickening, or adhesions about the gallbladder; delivering a cholecystokinin analogue intravenously to the human patient to enable the gallbladder to contract and to produce an ejection fraction of bile from the gallbladder during each contraction thereof, determining the degree of contraction of the gallbladder by means of measuring each the ejection fractions of the gallbladder; and analyzing the ejection fractions which are removed from the gallbladder to detect the presence or absence of calcium bilirubinate and/or cholesterol granules or crystals therein; whereby cholecystitis or microlithiasis of a gallbladder can be diagnosed with an accuracy or sensitivity of between about 90 to 98%, preferably 95 to 98%.

Using the method of the present invention cholecystitis or microlithiasis of a gallbladder in a human patient can be readily diagnosed if at least one of the following classifications are observed: (A) two major criteria, (B) one major and one minor criteria, and (C) three minor criteria, wherein the major criteria include: the presence of sludge or small stones in the gallbladder, and the finding of calcium bilirubinate granules or cholesterol crystals in the bile, and wherein the minor criteria comprises: gallbladder adhesions, cystic duct adhesions, decreased ejection fraction of the gallbladder of less than 35%, and focal gallbladder wall thickening of greater than 2 mm.

According to another embodiment of the present invention subtle cholecystitis or microlithiasis of a gallbladder may also be diagnosed by: inserting an endoscopic ultrasound device within the antrum of a stomach; positioning the endoscopic ultrasound device within the stomach such that the endoscopic ultrasound device is allowed to have a substantially unobstructed view of the gallbladder; activating the endoscopic ultrasound device such that it is capable of detecting whether the gallbladder exhibits any of the following: gallbladder sludge or small gallstones, focal wall thickening, or adhesions about the gallbladder and/or cystic duct; delivering magnesium sulfate intraluminally via the endoscopic ultrasound device to the patient in order to stimulate bile flow from the gallbladder by relaxing the biliary sphincter of oddi; and removing gallbladder bile and analyzing the gallbladder bile to detect the presence or absence of calcium bilirubinate and/or cholesterol granules or crystals therein; whereby cholecystitis or microlithiasis of a gallbladder can be diagnosed with an accuracy or sensitivity of between about 90% to 98%, preferably 95 to 98%.

The present invention also includes a method for diagnosing the cause of right upper quadrant abdominal pain in a patient having a gallbladder which is otherwise intact. This unique clinical protocol or diagnosis method comprises the following steps: (a) conducting a transabdominal ultrasound test, wherein if the transabdominal ultrasound test is positive then the patient would be a good candidate for a cholecystectomy and if normal then go to step (b); (b) conducting an oral cholecystography test to determined the concentrating ability of the gallbladder, wherein if the oral cholecystography test reveals a decreased concentrating ability then the patient would be a good candidate for a cholecystectomy and if normal then go to step (c); (c) conducting a combined endoscopic ultrasound and stimulated biliary drainage test if dietary and/or pharmaceutical therapy does not alleviate the right upper quadrant abdominal pain of the patient, wherein if the combined endoscopic ultrasound and stimulated biliary drainage test is positive then the patient would be a good candidate for a cholecystectomy and if normal then go to step (d); (d) conducting an endoscopic retrograde cholangiography (ERCP) test to determine whether any gallstones are present in the common bile duct, wherein if any gallstones are present then the patient would be a good candidate for a either an endoscopic sphincterotomy or a cholecystectomy and if no gallstones are present then go to step (e); and (e) conducting a sphincter of oddi manometry test to determine if there is elevated sphincter of oddi basal pressure, wherein if there is at least 40 mm of mercury sphincter of oddi pressure then the patient would be a good candidate for an endoscopic sphincterotomy and if less than 40 mm of mercury then the candidate would be a good candidate for dietary and/or pharmaceutical therapy.

The clinical protocol further comprising the steps of: (f) conducting a liver function test, wherein if normal then go to step (a) and if the liver function test is suggestive of biliary stasis then go to step (g); (g) conducting a combined endoscopic ultrasound and stimulated biliary drainage test, wherein if the combined endoscopic ultrasound and stimulated biliary drainage test is positive then the patient would be a good candidate for a cholecystectomy and if normal then go to step (h); (h) conducting an ERCP test to determine whether any gallstones are present in the common bile duct, wherein if any gallstones are present then the patient would be a good candidate for a either an endoscopic sphincterotomy or a cholecystectomy and if no gallstones are present then go to step (i); and (i) conducting a sphincter of oddi manometry test to determine if there is elevated sphincter of oddi basal pressure, wherein if there is at least 40 mm of mercury sphincter of oddi pressure then the patient would be a good candidate for an endoscopic sphincterotomy and if less than 40 mm of mercury then the candidate would be a good candidate for dietary and/or pharmaceutical therapy.

DESCRIPTION OF THE PREFERRED EMBODIMENTS

Figure 1:
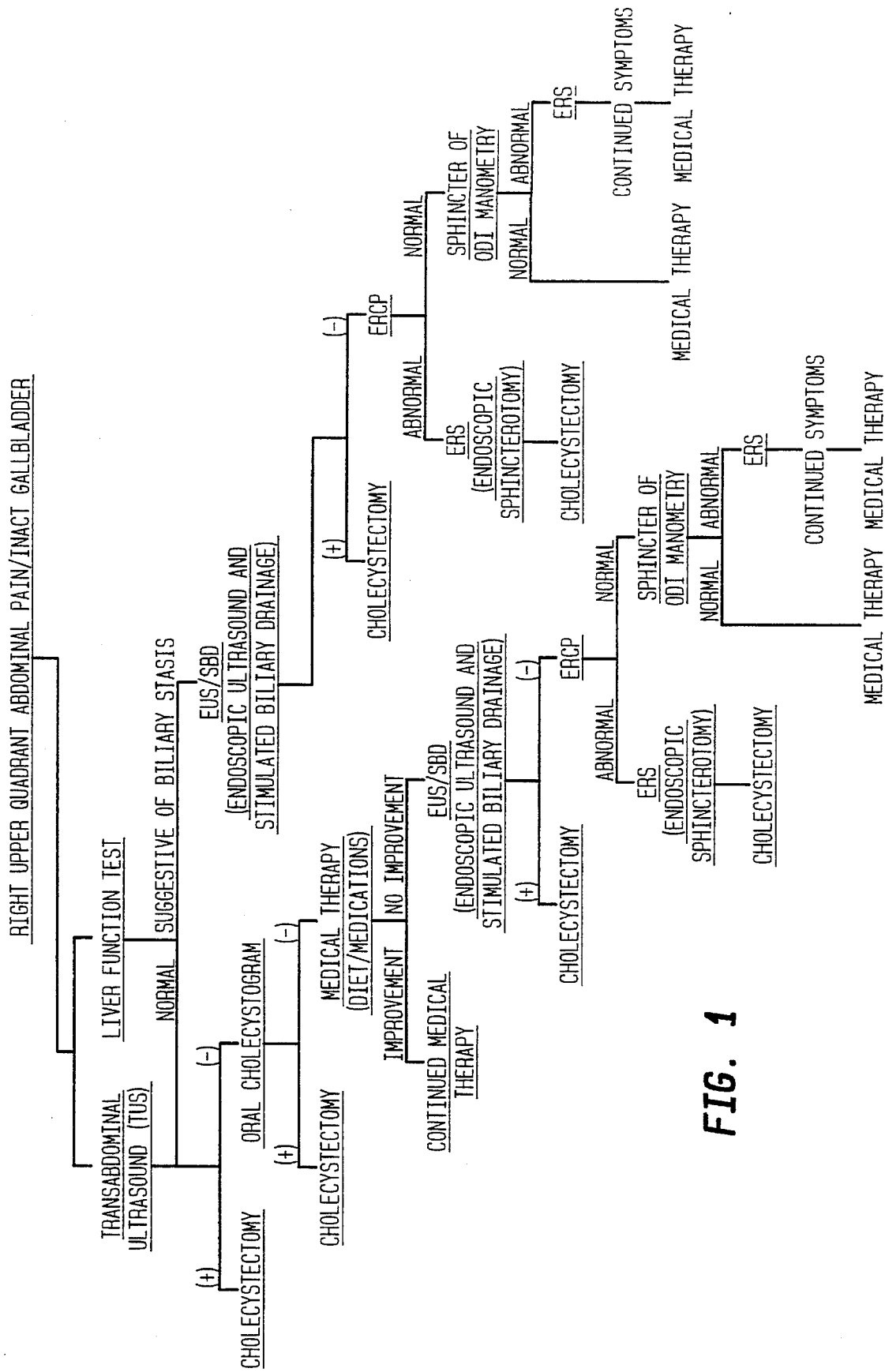
FIG. 1 is a flow chart depicting the clinical protocol to be taken using the diagnostic method of the present invention when a patient is experiencing right upper quadrant abdominal pain and the gallbladder otherwise appears intact.

To effectively diagnose and treat right upper quadrant abdominal pain, a logical protocol such as that developed by the present inventors can be quite helpful. The protocol of the present invention as shown in FIG. 1 is not only cost effective but includes the most accurate and up-to-date diagnostic technology. One such technology is endoscopic ultrasound (EUS). EUS has been shown to have superior diagnostic accuracy over conventional methods in a number of areas including gastrointestinal cancer staging. More recently EUS has been shown to have a high diagnostic accuracy in the diagnosis of cholecystitis and microlithiasis when transabdominal ultrasound is negative. The present inventors have developed a method using the combined EUS and stimulated biliary drainage brought about by the intravenous injection of a cholecystokinin analogue such as Kinevac™ which correctly diagnosed cholecystitis preoperatively in 20 out of 21 patients with biliary type pain and negative transabdominal ultrasound.

The protocol for right upper quadrant abdominal pain according to the present invention starts with good clinical history taking. The characteristics of the pain can help direct the initial steps. Pain that is epigastric, or right upper quadrant, that may radiate to the right subscapular area, and which is episodic is for example consistent with a gallbladder source. Such pain would be severe at times and may occur post prandially. A similar pain pattern could also be caused by biliary dyskinesia.

If the initial history is compatible with gallbladder disease, then the first tests performed should include a transabdominal ultrasound and liver functions tests. When the transabdominal ultrasound (TUS) is positive for cholelithiasis, the patients who are good surgical candidates should be considered for cholecystectomy. This will usually be accomplished by the laparoscopic approach. In the case of a normal TUS, the next diagnostic test, also utilizing conventional and widely available technology, is an oral cholecystogram. Oral cholecystography while not as sensitive for cholelithiasis as TUS, has the ability to determine gallbladder concentrating ability. If the oral cholecystogram reveals decreased concentrating ability (is non-visualizing) particularly with the double dose study, this would be an indication for cholecystectomy.

Many patients will have a negative TUS and oral cholecystogram, as well as normal liver function tests, but will continue with right upper quadrant abdominal pain. The irritable bowel syndrome (IBS) can at times mimic gallbladder disease. Patients with negative radiographic and ultrasound studies should be treated with the usual measures such as diet and/or antispasmodic medication in an attempt to resolve their symptoms which may be due to IBS. A response to these measures would support a diagnosis of pain due to the IBS and the diagnostic evaluation would be complete at this point.

If there was no response to treatment measures directed at IBS, the next diagnostic step indicated would be EUS combined with stimulated biliary drainage, utilizing a cholecystokinin (CCK) analogue intravenously, in accordance with the method of the present invention. This combination increases the accuracy of EUS by allowing observation of the degree of gallbladder contraction, as well as the collection of bile for microscopic examination. Positive EUS findings include the visualization of gallbladder sludge or small stones, as well as such features as focal wall thickening and gallbladder or cystic duct adhesions. A positive biliary drainage, which by itself may indicate cholecystitis, would be the finding of cholesterol crystals, or calcium bilirubinate granules in bile aspirated from the duodenum. The administration of intravenous cholecystokinin analogues such as sincalide also allows observation of gallbladder ejection fractions, similar to those obtained with CCK stimulated nuclear scintigraphy. An abnormal ejection fraction would be defined as less than 35% with the range of 35–40% being equivocal.

If combined endoscopic ultrasound and stimulated biliary drainage is positive, the patient would be at that point a candidate for cholecystectomy. Some patients, however, will remain with continuing episodes of right upper quadrant abdominal pain and negative combined EUS and stimulated biliary drainage studies.

These patients with totally negative studies and lack of response to dietary manipulation and antispasmodic medication, represent a challenge. This is a place in the protocol where ERCP may be helpful.

ERCP may reveal stones in the common bile duct to be a possible cause of the patient's pain. The common bile duct stones would next be extracted, possibly following an endoscopic sphincterotomy procedure (ERS). If patients with bile duct stones have not undergone cholecystectomy, that treatment would be indicated at this point for good surgical candidates. This is because the gallbladder would have been the most likely source for that patient's bile duct stone, or stones. If TUS, combined EUS and biliary drainage, and ERCP are all negative, Sphincter of Oddi Manonmetry (SOM) would then be indicated. A finding of elevated Sphincter of Oddi basal pressure on SOM (greater than 40 mm of mercury) is an indication that an endoscopic sphincterotomy procedure should be conducted in an attempt to relief the patient's pain. SOM would not be performed earlier in the protocol because of the risk of pancreatitis, ranging from three to about ten percent, associated with this procedure.

If the patient has continued pain following an endoscopic sphincterotomy, or after a negative SOM, medical therapy would again be indicated.

The right half of the protocol as shown in FIG. 1 indicates the diagnostic and therapeutic directions to be taken when liver function tests are suggestive of biliary stasis. In the presence of abnormal liver function tests and a negative TUS, there is again an indication for combined endoscopic ultrasound and stimulated biliary drainage, utilizing a CCK analogue delivered intravenously. From that point forward, the right side of the protocol duplicates that part of the left side of the protocol that begins with combined endoscopic ultrasound and stimulated biliary drainage, utilizing a CCK analogue delivered intravenously. This treatment protocol has the potential of directing diagnostic and therapeutic intervention for right upper quadrant abdominal pain in an economical manner. The use of combined endoscopic ultrasound and stimulated biliary drainage as describe in the present invention has the potential for actually decreasing the total medical cost for such patients. In this situation, the application of new technology can actually be cost effective.

The combined endoscopic ultrasound and stimulated biliary drainage, utilizing a CCK analogue delivered intravenously, involves the following steps: inserting an endoscopic ultrasound device within the antrum of a stomach; positioning the endoscopic ultrasound device within the stomach such that the endoscopic ultrasound device is allowed to have a substantially unobstructed view of the gallbladder; activating the endoscopic ultrasound device such that it is capable of detecting whether the gallbladder exhibits any of the following: gallbladder sludge or small gallstones, focal wall thickening, or adhesions about the gallbladder or cystic duct; delivering a cholecystokinin (CCK) analogue intravenously to the patient to enable the gallbladder to contract and to produce an ejection fraction of bile from the gallbladder during each contraction thereof, determining the degree of contraction of the gallbladder by means of measuring each the ejection fraction of the gallbladder; and analyzing the ejection fractions which are removed from the gallbladder to detect the presence or absence of calcium bilirubinate and/or cholesterol granules or crystals therein; whereby cholecystitis or microlithiasis of a gallbladder can be diagnosed with an accuracy or sensitivity of between about 90 to 98%. preferably 95 to 98%.

The cholecystokinin analogue is preferably sincalide, such as Kinevac™ which is manufactured by Bristol-Myers/Squibb. The cholecystokinin analogue is administered intravenously in a dosage of about 0.02 to 0.04 micrograms per killigram of weight of the recipient patient. Sincalide is the synthetic C-terminal octapeptide of the hormone cholecystokinin (choiescystokinin-pancreozymin, pancreozymin). It is designated chemically as L-aspartyl-L-tyrosyl-L-methionylglycyl-L-tryptophyl-L-methlonyl-L-aspartylphenyl-L-alaninamide hydrogen sulfate (ester). It is well known to use sincalide to stimulate the gallbladder to provide a sample of gallbladder bile that may be aspirated from the duodenum for determination of its composition including cholesterol saturation, calcium bilirubinate crystals, bile-stained epithelial cells, and bacteria. See U.S. Pat. No. 3,937,819 (Ondetti et al.), which issued on Feb. 10, 1976, and which is incorporated herein by reference.

It is also possible to combine endoscopic ultrasound with endoscopic Meltzer-Lyon testing in the diagnosis of cholecystitis and microlithiasis to an accuracy of about 90 to 98%, preferably 95 to 98%. The Meltzer-Lyon test differs from the previously discussed stimulated biliary drainage due to its use of magnesium sulfate versus the administration of cholecystokinin analogue intravenously. According to this method, the endoscopic ultrasound procedure discussed above would be followed by the Meltzer-Lyon test. The Meltzer-Lyon test is performed by advancing an endoscope to the second portion of the duodenum and then collecting bile, after stimulating bile flow from the gallbladder by relaxing the biliary sphincter of oddi by means of magnesium sulfate intraluminally infused through the endoscope. The bile is then removed and examined for cholesterol crystals and white blood cells, etc. The preferred dosage of magnesium sulfate is about 30 cc.

The CCK analogue delivered intravenously has been discovered to cause the gallbladder to contract while also promoting bile ejection fractions. A bile ejection fraction is the percentage of the gallbladder volume or contents that is ejected from the gallbladder during each contraction. Preferably, a microprocessor is included in the ultrasound console in order to measure each ejection fraction of the gallbladder, thereby determining the degree of contraction of the gallbladder. One such microprocessor is for example contained in an EUB-515 Ultrasound System, sold by Hitachi Medical Corporation of America. The EUB-515 Ultrasound System utilizes image processing algorithms coupled with high precision beam focusing technology, variable aperture dynamic focusing, and extended active aperture high density curved array transducers to deliver doppler and color flow mapping required for diagnosing gallbladder diseases. This endoscopic ultrasound device comprises a transducer which is capable of both transmitting and receiving ultrasonic signals.

The endoscopic ultrasound device generates a transmitted ultrasonic signal which passes through a high density probe such as a Pentax® FG-32UA ultrasound endoscope such that the ultrasonic signal comes into contact with the gallbladder and then returns to the endoscopic ultrasound device as a received ultrasonic signal. The received ultrasonic signal is sent to a signal processor where it is converted to a digitized signal and then sent to a microprocessor. The microprocessor is connected to a video monitor which displays a visual computerized image of the gallbladder, wherein the gallbladder sludge or small gallstones, focal wall thickening, or adhesions about the gallbladder and/or cystic duct can be detected.

It is preferable that the ultrasound endoscopic device in the stomach be positioned or placed such that the endoscopic ultrasound probe is allowed to have a substantially unobstructed view of the gallbladder. The placement within the stomach is typically accomplished by pressing a water filled balloon against the stomach wall.

Utilizing the Pentax® endoscopic ultrasound probe the present inventors have been able to see the cystic duct which was previously rarely ever seen. In this regard, the present inventors have noticed an area of increased density (i. e., an area that is hyperechoic by ultrasound criteria) surrounding the cystic duct in patients who were found to have cystic duct adhesions after surgery. The significance of this finding is that cystic duct adhesions may be one of the major mechanisms for pain in patients with cholecystitis.

Additionally, an aspiration device (e.g., hospital wall suction) is connected to the ultrasound endoscopic suction channel in order to removed ejection fractions of the bile from the gallbladder. The aspiration device is typically disposed in the second portion of the patient's duodenum. The ejection fractions of bile are then examined via an electronic or optical microscope to determine whether calcium bilirubinate and/or cholesterol granules or crystals are contained within the bile ejection fractions.

Using the combined endoscopic ultrasound and stimulated biliary drainage with an intravenously delivered CCK analogue, cholecystitis or microlithiasis of a gallbladder in a human patient may be successfully diagnosed in 90% to 98% of all patients tested if at least one of the following abnormalities is detected: a focal wall thickening in the range between about 2 to 4 mm, adhesions about the gallbladder and/or cystic duct, decreased ejection fractions of the gallbladder in the range between about 35 to 40%, and detection of calcium and/or cholesterol granules or crystals within the bile ejection fractions.

The present inventors have also developed a scoring system in an effort to standardize the diagnosis of cholecystitis using the combined EUS and stimulated biliary drainage with an intravenously delivered CCK analogue. A relatively high percentage of the accuracy of the method according to the present invention has been dependent on either the endoscopic visualization of small amounts of sludge, or the finding of calcium bilirubinate granules, or cholesterol crystals, with the intravenous CCK analogue stimulated biliary drainage. The finding of small amounts of sludge in the gallbladder can be difficult for a physician who is not experienced with this particular technique and the total accuracy of the procedure would either be decreased without significant experience, or even increased artificially if artifacts in the gallbladder were mistaken for sludge, which is an equally common error in the interpretation of this finding.

Because of this there is a need for a more standardized scoring system for the positive findings in EUS of the gallbladder, combined with the results of biliary drainage. Using the scoring system of the present inventors would provide a more reproducible result when the method of the present invention is performed by other physicians and would avoid erroneous diagnosis of cholecystitis.

The scoring system involves the evaluation of major criteria and minor criteria. Major criteria include (1) the presence of sludge or small stones (i.e., 0.5 to 2 mm) in the gallbladder, and (2) the finding of calcium bilirubinate granules or cholesterol crystals in the bile ejection fractions. Minor criteria include (1) gallbladder adhesions, (2) cystic duct adhesions, (3) decreased ejection fraction of the gallbladder of less than 35%, and (4) focal gallbladder wall thickening of greater than 2 mm. According to the scoring system of the present invention a positive diagnosis of cholecystitis can be made if any of the following combinations occur: (1) two major criteria are observed, (2) one major and one minor criteria are observed, or (3) three minor criteria are observed.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A method for diagnosing subtle cholecystitis or microlithiasis of a gallbladder in a patient which comprises the following steps:

inserting an endoscopic ultrasound device within the antrum of a stomach;

positioning said endoscopic ultrasound device within said stomach such that said endoscopic ultrasound device is allowed to have a substantially unobstructed view of said gallbladder;

activating said endoscopic ultrasound device such that it is capable of detecting whether said gallbladder exhibits any of the following: gallbladder sludge or small gallstones, focal wall thickening, or adhesions about said gallbladder and/or cystic duct;

delivering a cholecystokinin analogue intravenously to said patient to enable said gallbladder to contract and to produce an ejection fraction of bile from said gallbladder during each contraction thereof;

determining the degree of contraction of said gallbladder by means of measuring each said ejection fraction of said gallbladder; and removing said ejection fractions from said patient and analyzing said ejection fractions to detect the presence or absence of calcium bilirubinate and/or cholesterol granules or crystals therein.

2. The method according to claim 1 wherein said cholecystokinin analogue is sincalide.

3. The method according to claim 1 wherein said cholecystokinin analogue is administered in a dosage of about 0.02 to 0.04 micrograms per kilogram of weight of said patient.

4. The method according to claim 1 wherein said ejection fraction of said gallbladder is the percentage of the gallbladder volume or contents that is ejected from said gallbladder during each contraction.

5. The method according to claim 4 wherein said means of measuring each said ejection fraction of said gallbladder and thus determining the degree of contraction of said gallbladder is a microprocessor.

6. The method according to claim 1 wherein said endoscopic ultrasound device generates a transmitted ultrasonic signal which comes into contact with said gallbladder and then returns to said endoscopic ultrasound device as a received ultrasonic signal.

7. The method according to claim 6 wherein said endoscopic ultrasound device comprises a transducer which is capable of both transmitting and receiving ultrasonic signals.

8. The method according to claim 6 wherein said received ultrasonic signal is sent to a signal processor where it is converted to a digitized signal and then sent to a microprocessor.

9. The method according to claim 8 wherein said microprocessor is connected to a video monitor which displays a visual computerized image of said gallbladder, wherein said gallbladder sludge or small gallstones, focal wall thickening, or adhesions about said gallbladder and/or cystic duct can be detected.

10. The method according to claim 1 wherein said ejection fractions of said bile are removed from said gallbladder by means of an aspiration device disposed within said second portion of the duodenum.

11. The method according to claim 10 wherein the presence or absence of calcium bilirubinate and/or cholesterol granules or crystals contained within said removed bile is detected by means of an electronic or optical microscope.

12. The method according to claim 1 wherein said endoscopic ultrasound device within said stomach is positioned such that said endoscopic ultrasound device is allowed to have a substantially unobstructed view of said gallbladder by means of pressing a water filled balloon against the stomach wall.

13. The method according to claim 1 wherein cholecystitis or microlithiasis of a gallbladder in a human is diagnosed if at least one of the following criteria classifications are observed: (A) two major criteria, (B) one major and one manor criteria, and (C) three minor criteria, wherein said major criteria comprises: the presence of sludge or small stones in said gallbladder, and the finding of calcium bilirubinate granules or cholesterol crystals in said bile, and wherein said minor criteria comprises: gallbladder adhesions, cystic duct adhesions, decreased ejection fraction of the gallbladder of less than 35%, and focal gallbladder wall thickening of greater than 2 mm.

14. A method for diagnosing the cause of right upper quadrant abdominal pain in a patient having a gallbladder which is substantially intact comprises the following steps:

(a) conducting a transabdominal ultrasound test, wherein if said transabdominal ultrasound test is positive then the patient would be a good candidate for a cholecystectomy and if normal then go to step (b);

(b) conducting an oral cholecystography test to determined the concentrating ability of said gallbladder, wherein if said oral cholecystography test reveals a decreased concentrating ability then the patient would be a good candidate for a cholecystectomy and if normal then go to step (c);

(c) conducting a combined endoscopic ultrasound and stimulated biliary drainage, utilizing an intravenously delivered cholecystokinin analogue, test if dietary and/or pharmaceutical therapy does not alleviate the right upper quadrant abdominal pain of said patient, wherein if said combined endoscopic ultrasound and stimulated biliary drainage test is positive then said patient would be a good candidate for a cholecystectomy and if normal then go to step (d);

(d) conducting an endoscopic retrograde cholangiography test to determine whether any gallstones are present in the common bile duct, wherein if any gallstones are present then said patient would be a good candidate for a either an endoscopic sphincterotomy or a cholecystectomy and if no gallstones are present then go to step (e); and (e) conducting a sphincter of oddi manometry test to determine if there is elevated sphincter of oddi basal pressure, wherein if there is at least 40 mm of mercury sphincter of oddi pressure then said patient would be a good candidate for an endoscopic sphincterotomy and if less than 40 mm of mercury then the candidate would be a good candidate for dietary and/or pharmaceutical therapy.

15. The method according to claim 14 further comprising the steps of:

(f) conducting a liver function test, wherein if normal then go to step (a) and if said liver function test is suggestive of biliary stasis then go to step (g);

(g) conducting a combined endoscopic ultrasound and stimulated biliary drainage, utilizing an intravenously delivered cholecystokinin analogue, test, wherein if said combined endoscopic ultrasound and stimulated biliary drainage test is positive then said patient would be a good candidate for a cholecystectomy and if normal then go to step (h);

(h) conducting an endoscopic retrograde cholangiography test to determine whether any gallstones are present in the common bile duct, wherein if any gallstones are present then said patient would be a good candidate for a either an endoscopic sphincterotomy or a cholecystectomy and if no gallstones are present then go to step (i); and (i) conducting a sphincter of oddi manometry test to determine if there is elevated sphincter of oddi basal pressure, wherein if there is at least 40 mm of mercury sphincter of oddi pressure then said patient would be a good candidate for an endoscopic sphincterotomy and if less than 40 mm of mercury then the candidate would be a good candidate for dietary and/or pharmaceutical therapy.

16. The method according to claim 15 wherein said combined endoscopic ultrasound and stimulated biliary drainage test comprises the following steps:

inserting an endoscopic ultrasound device within the antrum of a stomach;

positioning said endoscopic ultrasound device within said stomach such that said endoscopic ultrasound device is allowed to have a substantially unobstructed view of said gallbladder;

activating said endoscopic ultrasound device such that it is capable of detecting whether said gallbladder exhibits any of the following: gallbladder sludge or small gallstones, focal wall thickening, or adhesions about said gallbladder and/or cystic duct;

delivering a cholecystokinin analogue intravenously to said human to enable said gallbladder to contract and to produce an ejection fraction of bile from said gallbladder during each contraction thereof;

determining the degree of contraction of said gallbladder by means of measuring each said ejection fraction of said gallbladder; and removing said ejection fractions from said patient and analyzing said ejection fractions to detect the presence or absence of calcium bilirubinate and/or cholesterol granules or crystals therein.

17. The method according to claim 16 wherein said cholecystokinin analogue is sincalide.

18. The method according to claim 16 wherein said cholecystokinin analogue is administered in a dosage of about 0.02 to 0.04 micrograms per kilogram of weight of said patient.

19. The method according to claim 16 wherein said ejection fraction of said gallbladder is the percentage of the gallbladder volume or contents that is ejected from said gallbladder during each contraction.

20. The method according to claim 19 wherein said means of measuring each said ejection fraction of said gallbladder and thus determining the degree of contraction of said gallbladder is a microprocessor.

21. The method according to claim 16 wherein said endoscopic ultrasound device generates a transmitted ultrasonic signal which comes into contact with said gallbladder and then returns to said endoscopic ultrasound device as a received ultrasonic signal.

22. The method according to claim 21 wherein said endoscopic ultrasound device comprises a transducer which is capable of both transmitting and receiving ultrasonic signals.

23. The method according to claim 21 wherein said received ultrasonic signal is sent to a signal processor where it is convened to a digitized signal and then sent to a microprocessor.

24. The method according to claim 23 wherein said microprocessor is connected to a video monitor which displays a visual computerized image of said gallbladder, wherein said gallbladder sludge or small gallstones, focal wall thickening, or adhesions about said gallbladder and cystic duct can be detected.

25. The method according to claim 16 wherein said ejection fractions of said bile are removed from said gallbladder by means of an aspiration device disposed within the second portion of the duodenum.

26. The method according to claim 25 wherein the presence or absence of calcium bilirubinate and/or cholesterol granules or crystals contained within said removed bile is detected by means of an electronic or optical microscope.

27. The method according to claim 16 wherein said endoscopic ultrasound device within said stomach is positioned such that said endoscopic ultrasound device is allowed to have a substantially unobstructed view of said gallbladder by means of pressing a water filled balloon against the stomach wall.

28. The method according to claim 16 wherein cholecystitis or microlithiasis of a gallbladder in said patient is diagnosed if at least one of the following criteria classifications are observed: (A) two major criteria, (B) one major and one minor criteria, and (C) three minor criteria, wherein said major criteria comprises: the presence of sludge or small stones in said gallbladder, and the finding of calcium bilirubinate granules or cholesterol crystals in said bile, and wherein said minor criteria comprises: gallbladder adhesions, cystic duct adhesions, decreased ejection fraction of the gallbladder of less than 35%, and focal gallbladder wall thickening of greater than 2 mm.

29. A method for diagnosing subtle cholecystitis or microlithiasis of a gallbladder in a patient which comprises the following steps:

inserting an endoscopic ultrasound device within the antrum of a stomach;

positioning said endoscopic ultrasound device within said stomach such that said endoscopic ultrasound device is allowed to have a substantially unobstructed view of said gallbladder;

activating said endoscopic ultrasound device such that it is capable of detecting whether said gallbladder exhibits any of the following: gallbladder sludge or small gallstones, focal wall thickening, or adhesions about said gallbladder and/or cystic duct;

delivering magnesium sulfate intraluminally via said endoscopic ultrasound device to said patient in order to stimulate bile flow from said gallbladder by relaxing the biliary sphincter of oddi; and removing gallbladder bile from said patient and analyzing said gallbladder bile to detect the presence or absence of calcium bilirubinate and/or cholesterol granules or crystals therein.

30. The method according to claim 29 wherein said gallbladder bile is removed by means of an aspiration device disposed within the second portion of the duodenum.

31. The method according to claim 29 wherein said magnesium sulfate is administered in a dosage of about 30 cc.

32. A method for diagnosing the cause of right upper quadrant abdominal pain in a patient having a gallbladder which is substantially intact comprises the following steps:

(a) conducting a transabdominal ultrasound test, wherein if said transabdominal ultrasound test is positive then the patient would be a good candidate for a cholecystectomy and if normal then go to step (b);

(b) conducting an oral cholecystography test to determined the concentrating ability of said gallbladder, wherein if said oral cholecystography test reveals a decreased concentrating ability then the patient would be a good candidate for a cholecystectomy and if normal then go to step (c);

(c) conducting a combined endoscopic ultrasound and stimulated biliary drainage, utilizing an intraluminally delivered magnesium sulfate, test if dietary and/or pharmaceutical therapy does not alleviate the right upper quadrant abdominal pain of said patient, wherein if said combined endoscopic ultrasound and stimulated biliary drainage test is positive then said patient would be a good candidate for a cholecystectomy and if normal then go to step (d);

(d) conducting an endoscopic retrograde cholangiography test to determine whether any gallstones are present in the common bile duct, wherein if any gallstones are present then said patient would be a good candidate for a either an endoscopic sphincterotomy or a cholecystectomy and if no gallstones are present then go to step (e); and (e) conducting a sphincter of oddi manometry test to determine if there is elevated sphincter of oddi basal pressure, wherein if there is at least 40 mm of mercury sphincter of oddi pressure then said patient would be a good candidate for an endoscopic sphincterotomy and if less than 40 mm of mercury then the candidate would be a good candidate for dietary and/or pharmaceutical therapy.

33. The method according to claim 32 further comprising the steps of:

(f) conducting a liver function test, wherein if normal then go to step (a) and if said liver function test is suggestive of biliary stasis then go to step (g);

(g) conducting a combined endoscopic ultrasound and stimulated biliary drainage, utilizing an intraluminally delivered magnesium sulfate, test, wherein if said combined endoscopic ultrasound and stimulated biliary drainage test is positive then said patient would be a good candidate for a cholecystectomy and if normal then go to step (h);

(h) conducting an endoscopic retrograde cholangiography test to determine whether any gallstones are present in the common bile duct, wherein if any gallstones are present then said patient would be a good candidate for a either an endoscopic sphincterotomy or a cholecystectomy and if no gallstones are present then go to step (i); and (i) conducting a sphincter of oddi manometry test to determine if there is elevated sphincter of oddi basal pressure, wherein if there is at least 40 mm of mercury sphincter of oddi pressure then said patient would be a good candidate for an endoscopic sphincterotomy and if less than 40 mm of mercury then the candidate would be a good candidate for dietary and/or pharmaceutical therapy.

34. The method according to claim 33 wherein said combined endoscopic ultrasound and stimulated biliary drainage test comprises the following steps:

inserting an endoscopic ultrasound device within the antrum of a stomach;

positioning said endoscopic ultrasound device within said stomach such that said endoscopic ultrasound device is allowed to have a substantially unobstructed view of said gallbladder;

activating said endoscopic ultrasound device such that it is capable of detecting whether said gallbladder exhibits any of the following: gallbladder sludge or small gallstones, focal wall thickening, or adhesions about said gallbladder and/or cystic duct;

delivering magnesium sulfate intraluminally via said endoscopic ultrasound device to said patient in order to stimulate bile flow from said gallbladder by relaxing the biliary sphincter of oddi; and removing gallbladder bile from said patient and analyzing said gallbladder bile to detect the presence or absence of calcium bilirubinate and/or cholesterol granules or crystals therein.

35. The method according to claim 34 wherein said gallbladder bile is removed from said gallbladder by means of an aspiration device disposed within the second portion of the duodenum.

36. The method according to claim 34 wherein said magnesium sulfate is administered in a dosage of about 30 cc.

* * * * *